(12) United States Patent
Clerc et al.

(10) Patent No.: US 9,814,608 B2
(45) Date of Patent: Nov. 14, 2017

(54) ANTI-MIGRATION STENT WITH QUILL FILAMENTS

(71) Applicant: Boston Scientific Scimed, Inc., Maple Grove, MN (US)

(72) Inventors: Claude O. Clerc, Marlborough, MA (US); Barry Weitzner, Acton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 620 days.

(21) Appl. No.: 14/227,501

(22) Filed: Mar. 27, 2014

(65) Prior Publication Data

US 2014/0214150 A1    Jul. 31, 2014

Related U.S. Application Data

(63) Continuation of application No. 13/536,110, filed on Jun. 28, 2012, now Pat. No. 8,715,334.

(60) Provisional application No. 61/507,819, filed on Jul. 14, 2011.

(51) Int. Cl.
| | |
|---|---|
| A61F 2/848 | (2013.01) |
| A61F 2/82 | (2013.01) |
| A61F 2/88 | (2006.01) |
| A61F 2/90 | (2013.01) |
| A61F 2/915 | (2013.01) |

(Continued)

(52) U.S. Cl.
CPC ............... *A61F 2/82* (2013.01); *A61F 2/848* (2013.01); *A61F 2/88* (2013.01); *A61F 2/90* (2013.01); *A61F 2/915* (2013.01); *A61F 2/07* (2013.01); *A61F 2/86* (2013.01); *A61F 2002/825* (2013.01); *A61F 2002/8483* (2013.01); *A61F 2002/8486* (2013.01); *A61F 2002/91575* (2013.01); *A61F 2210/0014* (2013.01); *A61F 2210/0057* (2013.01); *A61F 2220/005* (2013.01); *A61F 2220/0016* (2013.01); *A61F 2220/0058* (2013.01); *A61F 2230/0078* (2013.01); *A61F 2250/0026* (2013.01); *A61F 2250/0028* (2013.01); *A61F 2250/0039* (2013.01); *A61F 2250/0067* (2013.01); *A61F 2250/0096* (2013.01)

(58) Field of Classification Search
CPC ................ A61F 2/82–2/945; A61F 2002/8486
See application file for complete search history.

(56) References Cited

U.S. PATENT DOCUMENTS

| | | |
|---|---|---|
| 5,800,526 A | 9/1998 | Anderson et al. |
| 7,624,487 B2 | 12/2009 | Trull et al. |
| 7,722,666 B2 | 5/2010 | Lafontaine |

(Continued)

OTHER PUBLICATIONS

U.S. Appl. No. 61/507,819, filed Jul. 14, 2011: Inventors: Clerc et al.

*Primary Examiner* — Yashita Sharma
*Assistant Examiner* — Rebecca Preston
(74) *Attorney, Agent, or Firm* — Seager, Tufte & Wickhem, LLP

(57) ABSTRACT

A stent that includes a plurality of quill filaments. Each quill filament includes filament material, a surface, and a plurality of quills. Each quill has a tip, a body, and a base where the body extends from the base to the tip. The quill filaments can be interwoven to form the stent or the quill filaments can be engaged to the framework of a stent.

9 Claims, 6 Drawing Sheets

Figure 1:
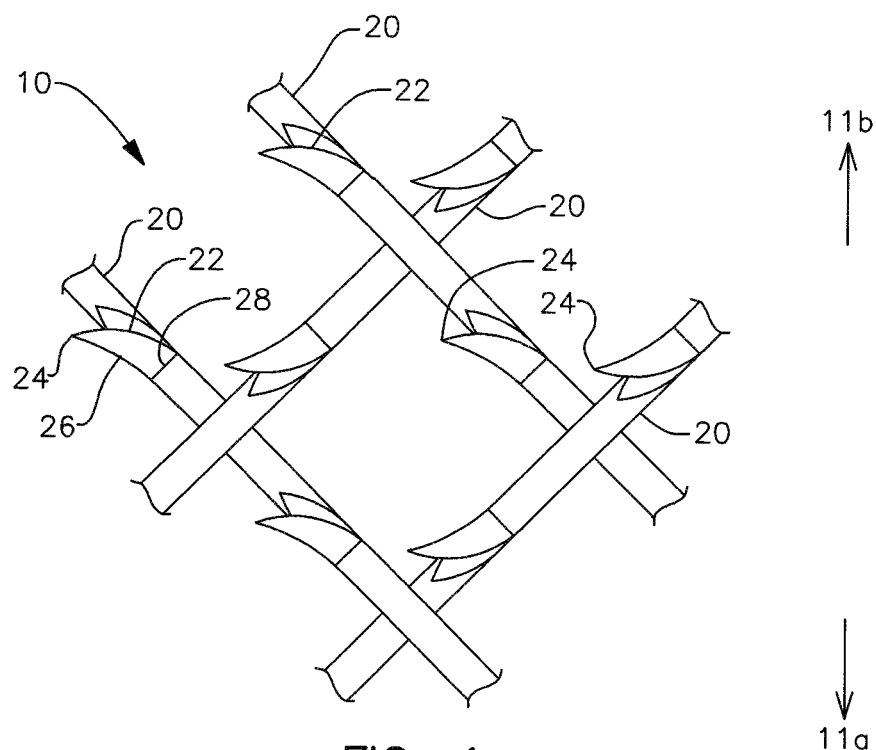

(51) Int. Cl.
*A61F 2/86* (2013.01)
*A61F 2/07* (2013.01)

(56) References Cited

U.S. PATENT DOCUMENTS

| | | |
|---|---|---|
| 7,806,908 B2 | 10/2010 | Ruff |
| 8,292,946 B2 | 10/2012 | Thistle et al. |
| 2004/0117004 A1 | 6/2004 | Osborne et al. |
| 2004/0162606 A1* | 8/2004 | Thompson ................. A61F 2/06 623/1.22 |
| 2004/0167605 A1* | 8/2004 | Elliott ....................... A61F 2/07 623/1.13 |
| 2005/0038503 A1* | 2/2005 | Greenhalgh .............. A61F 2/07 623/1.42 |
| 2007/0219587 A1* | 9/2007 | Accardo .......... A61B 17/06166 606/228 |
| 2008/0249598 A1 | 10/2008 | Sherry |
| 2009/0018577 A1 | 1/2009 | Leung et al. |
| 2009/0112236 A1* | 4/2009 | Stopek .................... A61L 17/12 606/151 |
| 2009/0149946 A1* | 6/2009 | Dixon ....................... A61F 2/07 623/1.36 |
| 2009/0259306 A1 | 10/2009 | Rowe |
| 2010/0294103 A1 | 11/2010 | Genova et al. |

\* cited by examiner

ANTI-MIGRATION STENT WITH QUILL FILAMENTS

CROSS-REFERENCE TO RELATED APPLICATIONS

This application is a continuation of U.S. application Ser. No. 13/536,110 which was filed Jun. 28, 2012; which claims priority to U.S. Application No. 61/507,819 which was filed Jul. 14, 2011; and which are each incorporated herein in its entirety by reference.

STATEMENT REGARDING FEDERALLY SPONSORED RESEARCH

Not applicable

BACKGROUND OF THE INVENTION

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. For example, the introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices are radially expandable endoprostheses which are typically intravascular implants capable of being implanted transluminally and enlarged radially after being introduced percutaneously or through a natural orifice. Stents may be implanted in a variety of body lumens or vessels such as within the vascular system, urinary tracts, bile ducts, fallopian tubes, coronary vessels, secondary vessels, gastrointestinal tract, airways, etc. They may be self-expanding, expanded by an internal radial force, such as when mounted on a balloon, or a combination of self-expanding and balloon expandable (hybrid expandable).

One of the main problems with stenting, especially with partially covered and fully covered stents, is migration. Though the exact reasons leading to stent migration are not well known, it is important to prevent stent migration for many reasons. The main reason is that if the stent moves away from the stenosis in which it was implanted, the vessel blockage may reoccur, also a migrated stent can cause problems for the patients. For instance a migrated duodenal stent can cause an obstruction of the small bowel. Migration can occur shortly after stent implantation or several months afterwards. Bare stents tends to have a lower migration rate than partially covered or fully covered stents because tissue grows through the stent mesh and keep the stent from moving. Several techniques are used to prevent stent migration, the main one is to use a flared end to anchor the stent at the stricture. However, there is still a significant amount of migration even with flared stents. Spikes or barbs have also been used to prevent stent migration.

In a few applications, it is also important to have a stent that can be retrieved after implantation, either immediately or even a few months after implantation. For instance, the stent may be used to treat a benign stenosis like a corrosive stricture of the esophagus. It is expected that the tissue would remodel under the constant pressure applied by the stent and therefore, the stent should be removed after a few weeks. Typically, esophageal stents would move downwards, therefore the stent should be designed to prevent downwards migration but allow for endoscopic removal through the mouth. Therefore it is important to have spikes of barbs oriented in one direction in order to prevent migration in one direction but allow for stent removal in the other direction.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

In at least one embodiment, the invention is directed to a stent comprising a plurality of interwoven quill filaments extending from a first end to a second end of the stent. Each quill filament comprises filament material, a surface, and a plurality of quills, each quill having a tip, a body, and a base, the body extending from the base to the tip. In at least one embodiment, at least one portion of the stent comprises quills. In some embodiments, the stent comprises a first end region, a second end region, and a middle region between the first and second end regions. In at least one embodiment, at least one of the first end region, the second end region, and the middle region of the stent comprises quills. In some embodiments, only the middle region of the stent comprises quills. In other embodiments, only the first and second end region of the stent comprises quills. In yet another embodiment, the first end region, the middle region, and the second end region each comprise quills. In some embodiments, the quills are each oriented in a first direction relative to the first end of the stent. In other embodiments, the quills are oriented in different directions relative to the first end of the stent. In one embodiment, the quills comprise first quills oriented in a first direction relative to the first end of the stent and second quills oriented in a second direction relative to the first end of the stent where the first and second directions are opposite directions.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described an embodiments of the invention.

BRIEF DESCRIPTION OF THE SEVERAL VIEWS OF THE DRAWING(S)

A detailed description of the invention is hereafter described with specific reference being made to the drawings.

Figure 2:
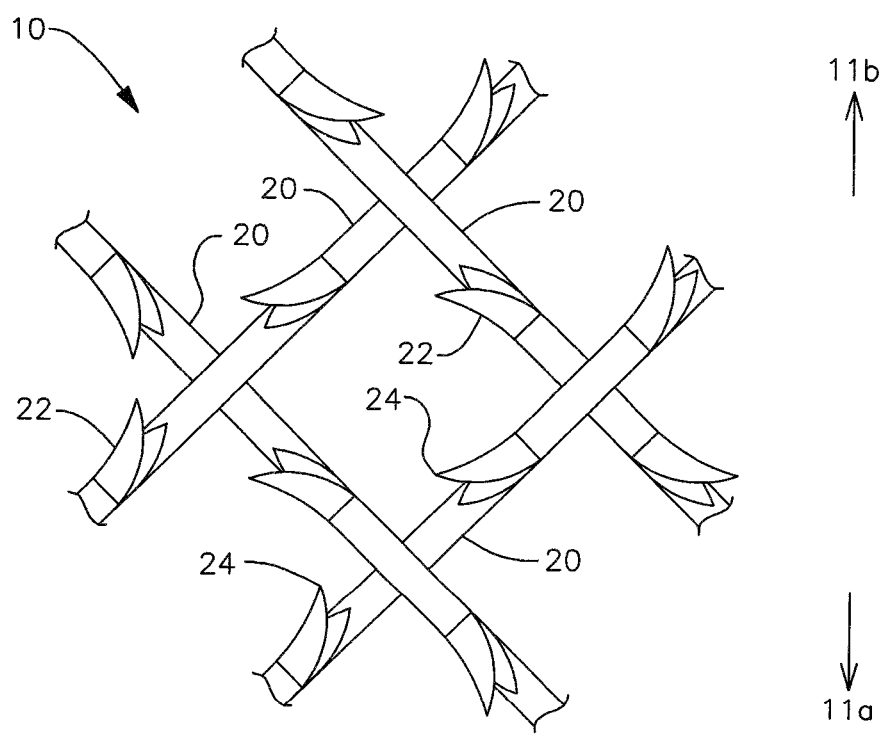
Figure 3:
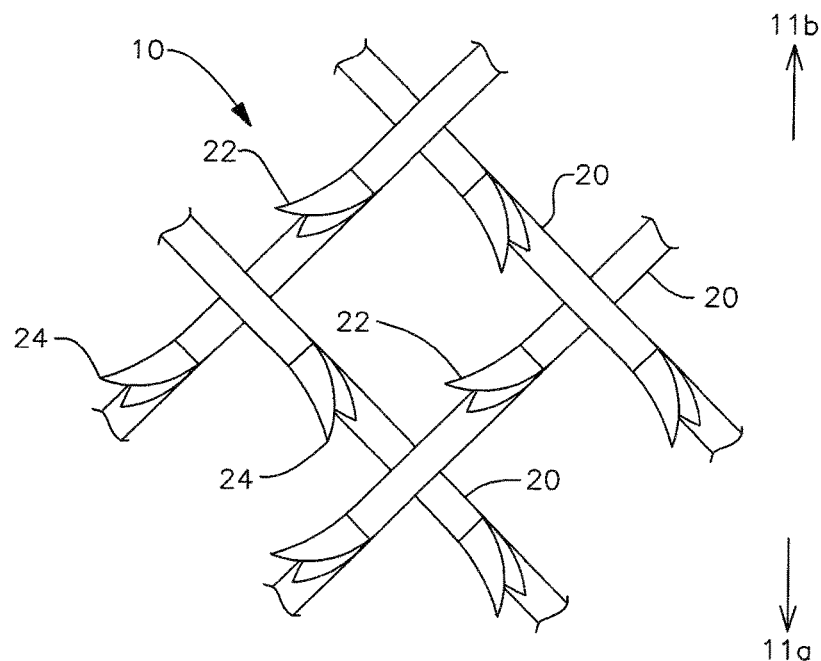
Figure 4:
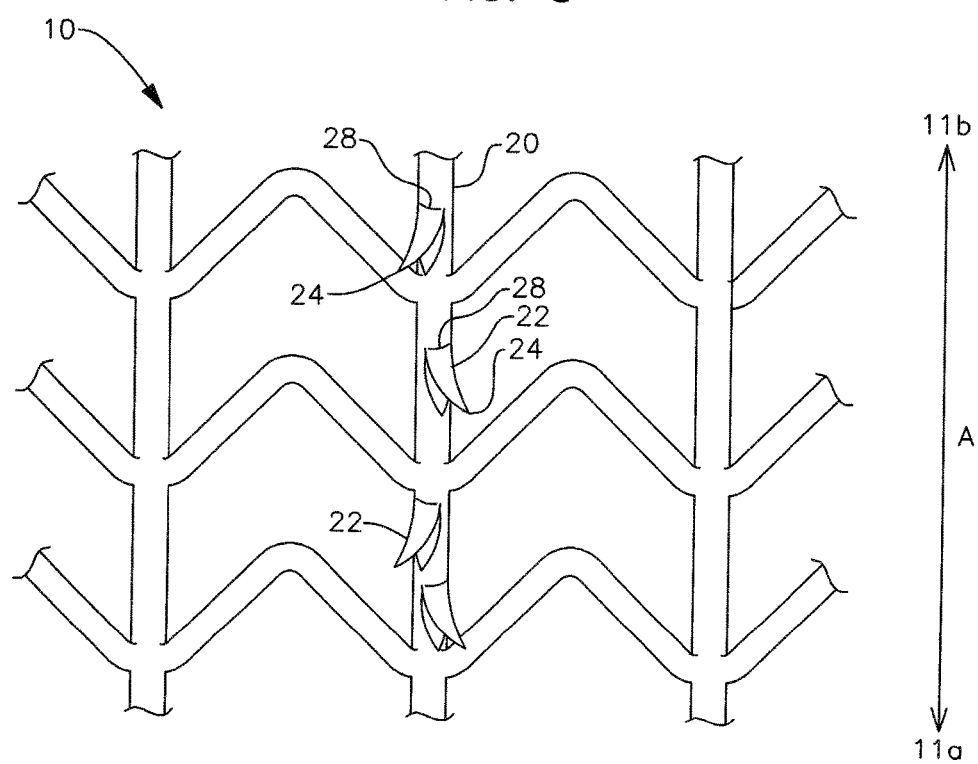
Figure 5:
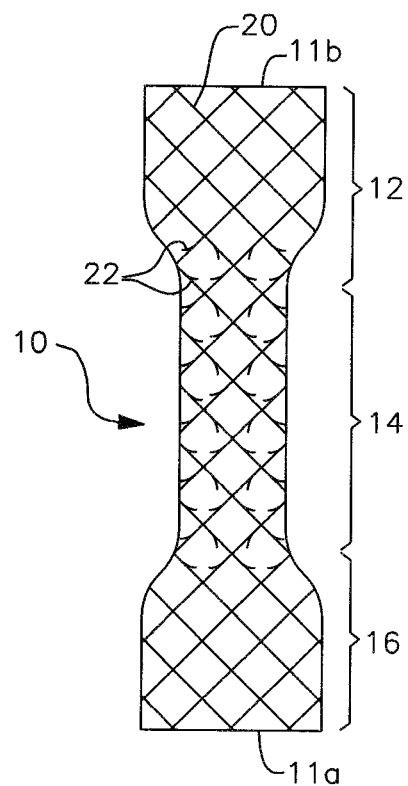
Figure 6:
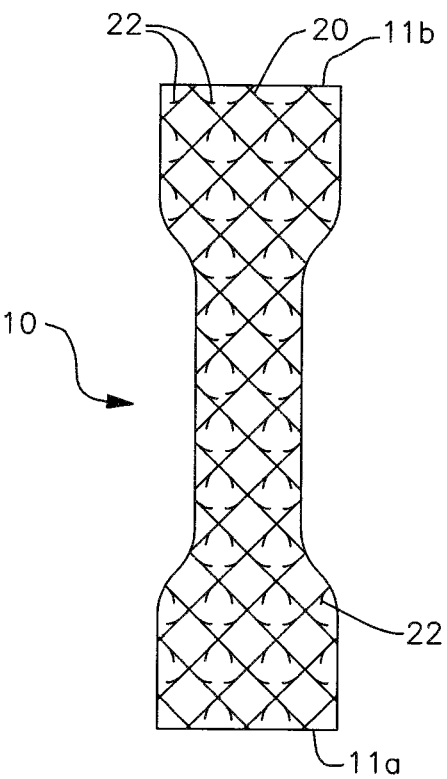
Figure 7:
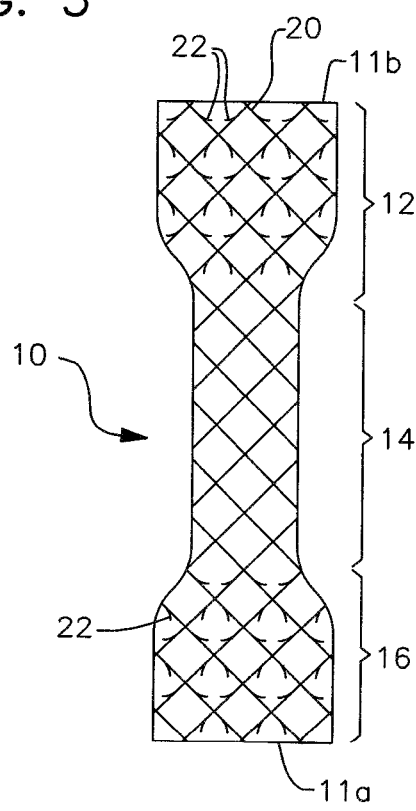
Figure 8:
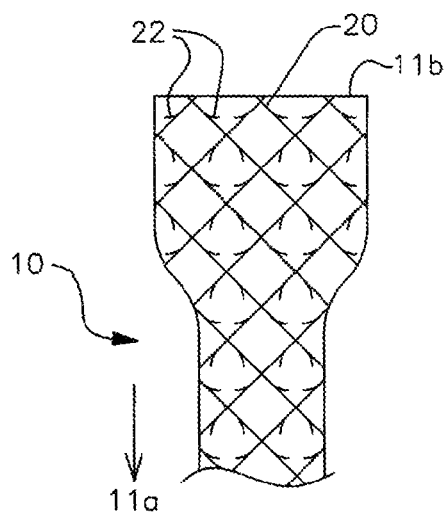
Figure 10:
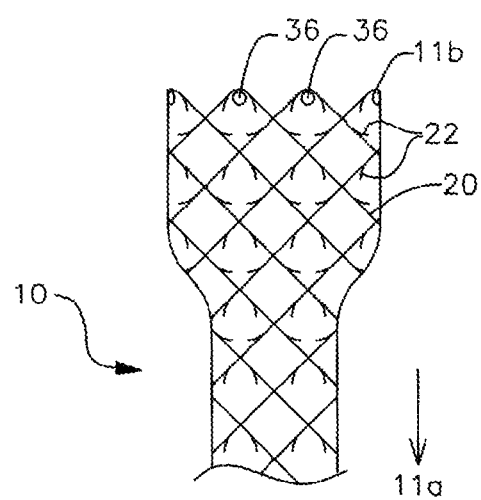
Figure 9:
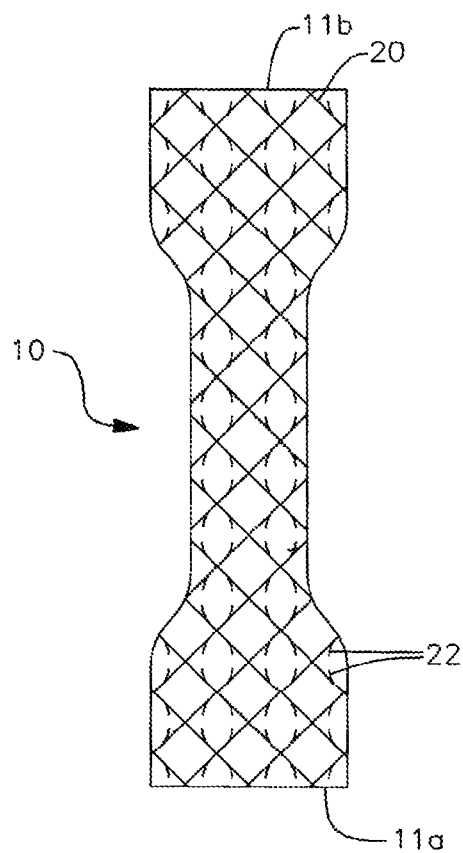
Figure 11:
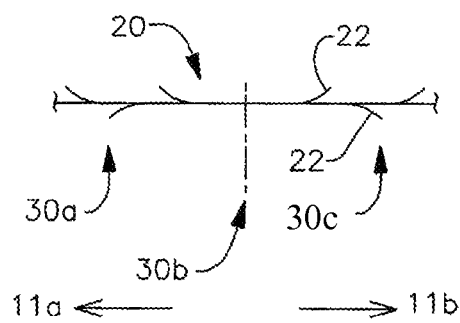
Figure 12:
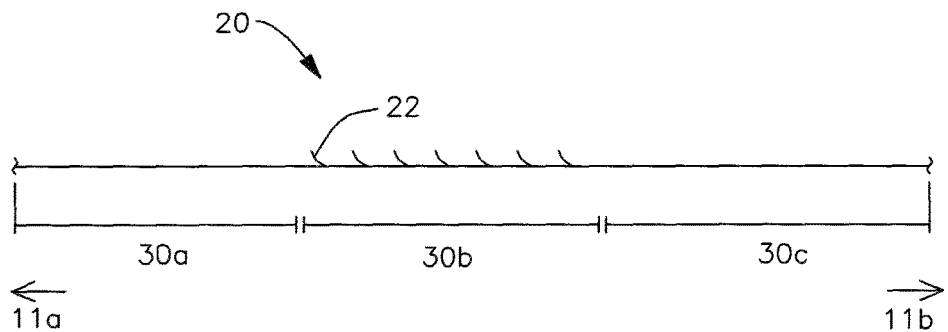
Figure 13:
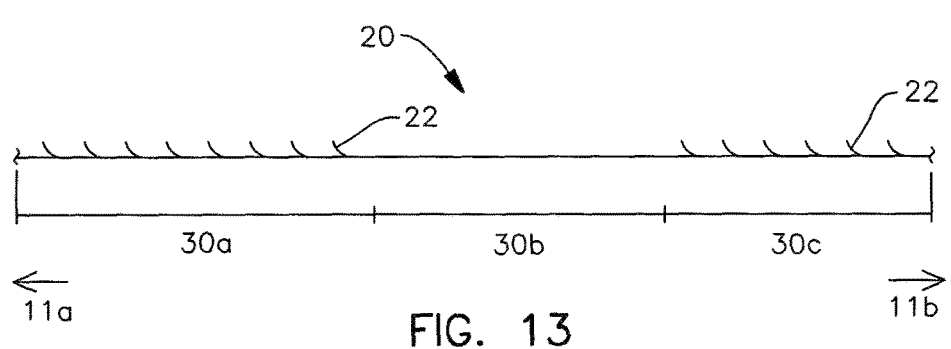
Figure 14:
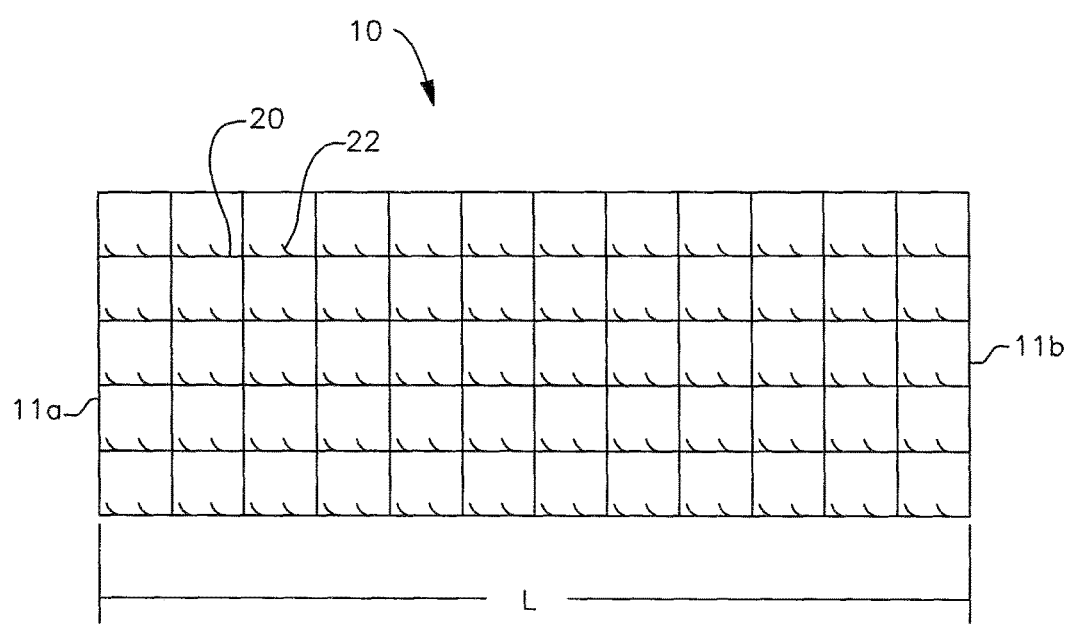
Figure 15:
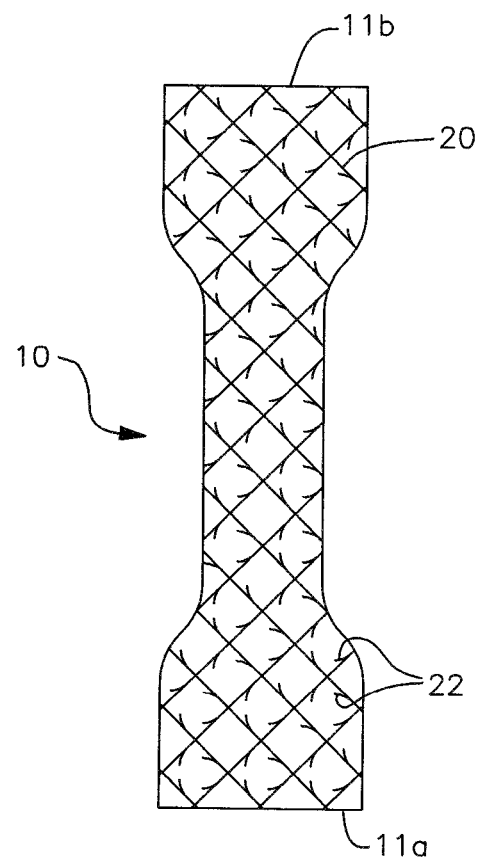
Figure 16:
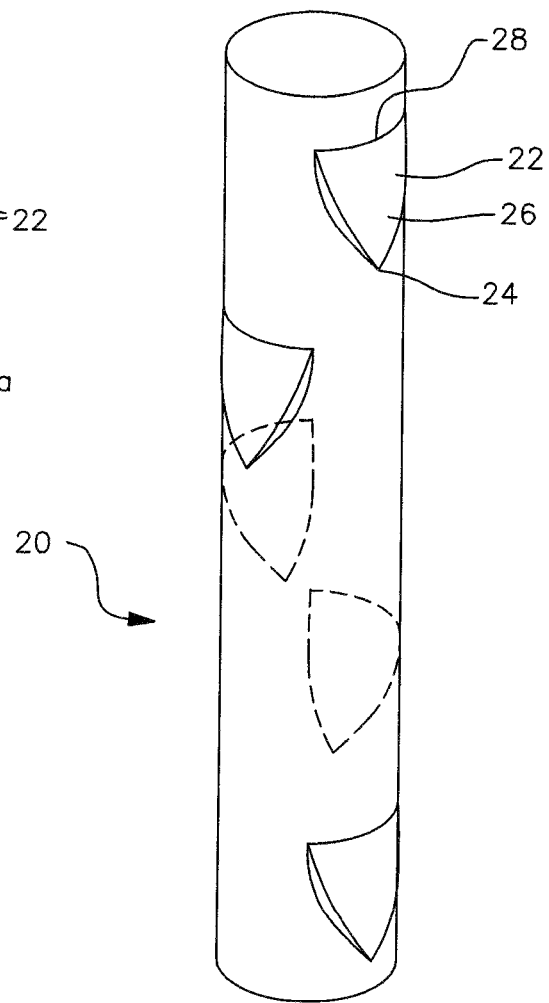

FIG. 1 is a view of interwoven filaments with quills.
FIG. 2 is a view of interwoven filaments with quills.
FIG. 3 is a view of interwoven filaments with quills.
FIG. 4 is a view of a portion of a stent with a filament with quills.
FIG. 5 is a schematic of a stent comprising filaments with quills.
FIG. 6 is a schematic of a stent comprising filaments with quills.
FIG. 7 is a schematic of a stent comprising filaments with quills.
FIG. 8 is a schematic of a portion of a stent comprising filaments with quills.
FIG. 9 is a schematic of a stent comprising filaments with quills.
FIG. 10 is a schematic of a portion of a stent comprising filaments with quills.
FIG. 11 is a schematic of a portion of a filament with quills.
FIG. 12 is a schematic of a quill filament.
FIG. 13 is a schematic of a quill filament.
FIG. 14 is a schematic of a stent comprising filaments with quills.
FIG. 15 is a schematic of a stent comprising filaments with quills.
FIG. 16 is a schematic of a portion of a quill filament.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

FIGS. 1-10 and 14-15 show a stent 10, or portion of a stent 10, that has at least one quill filament 20. A quill filament 20 as used in this application refers to a filament that has at least one quill or barb 22. A "filament" as used in this application encompasses a piece of material in the form of a wire, a strand, a suture, a thread, or a fiber. A "quill" or "barb" as used in this application is a portion of filament material that has been partially separated from the body of the filament so that the filament material forming the quill 22 is at an oblique angle relative to, and extends over, the body of the filament. For simplicity, the term "quill" will be used hereinafter. In some embodiments, the quill filament 20 has a substantially round cross-section with a diameter and a circumference. In one embodiment, a quill filament 20 with a substantially round cross-section has two sides, each side being half of the circumference of the quill filament 20. Suitable materials to form a quill filament 20 are discussed below. A non-limiting example of a product suitable as a quill filament includes the Quill™ Knotless Tissue Closure Device available from Angiotech.

In at least one embodiment, the stent 10 comprises a plurality of interwoven strands and at least one of the strands is a quill filament 20 with at least one quill 22. In some embodiments, all of the interwoven strands are quill filaments 20. FIGS. 1-10 and 14-15 provide non-limiting examples of a stent comprising a plurality of interwoven strands of quill filaments 20. In some embodiments, the quills 22 prevent migration of the stent 10 after placement in a body lumen. In this embodiment, longitudinal movement of the stent is prevented by the quills.

In some embodiments, the stent 10 has end regions 12, 16 with a larger diameter than the middle region 14. As used in this application a "region" is a section of the tubular stent that extends from a first longitudinal position to a second longitudinal position and extends around the entire circumference of the tubular stent. Thus, a region has a longitudinal length and includes the entire circumference of the tubular stent. Stents 10 with end regions 12, 16 that have a larger diameter than the middle region 14 are shown for example in FIGS. 5-10. In some embodiments, the stent has only one end region with a larger diameter than the middle region. In some embodiments at least one end region is flared. In other embodiments, at least one end region is a flange. As used in this application, a "flange" is a region of the stent that has a larger diameter than the adjacent region. It is within the scope of the invention for the stent to have any number of enlarged diameter regions at any location along the length of the stent. In other embodiments, the diameter of the stent is substantially the same along the length of the stent.

It is within the scope of the invention for any of the quill stent embodiments described below to include a graft (not shown) or a cover for a partially or fully covered stent. As used in this application, a "partially covered stent" has a graft that covers less than an entire surface (outer or inner) of the stent whereas a "fully covered stent" has a graft that covers an entire surface (outer or inner) of the stent. It is within the scope of the invention for the graft to be engaged to the outer surface of the stent, to the inner surface of the stent, or to both the outer surface and the inner surface of the stent. Quills positioned on at least a portion of the outer surface of the stent are used to engage a graft and/or are used to prevent migration of the stent. Quills positioned on the inner surface of the stent can also be used to engage a graft.

The disclosure of an exemplary method to form each of the stents shown in the figures should not be construed as limiting the scope of the invention. The stents disclosed herein can be made by any alternative suitable method, including but not limited to weaving, twisting, braiding, knotting, crocheting, and wrapping. Furthermore, different portion(s) of the stent can have quills other than the portions of the exemplary stents shown in the figures. For example in one embodiment not shown only one end region of the stent has quills. In another embodiment not shown, the stent has a plurality of quills in one end region and the middle region but no quills in the other end region. Additionally, the orientation/direction of the quills relative to an end of a stent in different regions of the stent can be different from the exemplary stents shown in the figures. Furthermore, the orientation of the quill filaments when woven, twisted, braided, knotted, crocheted, or wrapped to form the stent is not limited to the orientation provided in the exemplary method.

In some embodiments, the plurality of strands is interwoven using a discrete braiding process to form a stent. In this embodiment, the strands are looped at one end 11 of the stent and wound and welded or secured at the other extremity. In other embodiments, the plurality of strands is interwoven using a continuous braiding process. With the continuous braiding process, the individual stents are cut from a braid and do not have looped extremities. An example of a stent formed by interwoven quill filaments 20 interwoven using a discrete braiding process is shown for example in FIG. 10.

In one embodiment, the stent 10 shown in FIG. 5 is made with a plurality of quill filaments 20 using a continuous braiding method. An example of a quill filament 20 of the stent shown in FIG. 5 is shown in FIG. 12. As can be seen in FIG. 12, each quill filament 20 has a first zone 30*a* with no quills, a second zone 30*b* with quills 22 oriented in the same direction relative to one end 11*a* of the filament, and a third zone 30*c* with no quills, where the second zone is between and connects the first and the third zones. Each quill filament has the same alignment or orientation when incorporated into the stent. This method results in an interwoven stent 10 with a plurality of quills 22 oriented in the same direction relative to an end 11*a* of the stent 10, as shown in for example in FIG. 5. Additionally, as shown in FIG. 5, the stent 10 has quills 22 positioned only in the middle region 14 of the stent 10. FIG. 3 is an enlarged depiction of a portion of a stent 10 comprising interwoven quill filaments 20 where the quills 22 are oriented in the same direction relative to an end 11*a* of the stent 10. Thus, the tip 24 of each quill 22 is directed/oriented away from one end 11*b* of the stent and towards the other end 11*a* of the stent. A quill tip is directed/oriented towards an end 11 of the stent when the tip is at either a 90 degree angle to the end of the stent or when the tip is at an oblique angle between 0 and 180 degrees to the end of the stent.

In one embodiment, the stent 10 shown in FIG. 6 is made with a plurality of quill filaments 20 using a continuous braiding method where each quill filament has a plurality of quills 22 along the length of the filament; each quill 22 on a filament is facing the same direction; and the quill filaments each have the same orientation when incorporated into the stent. This method results in an interwoven stent with a plurality of quills 22 oriented in the same direction relative to an end 11*a* of the stent 10, as shown for example in FIG. 6 and in the enlarged depiction of FIG. 3, as discussed above. Also as shown in FIG. 6, the entire stent has quills 22, as opposed to only a portion of the stent.

In one embodiment, the stent 10 shown in FIG. 7 is made by continuous braiding method using a plurality of quill filaments 20. An example of a quill filament 20 of the stent shown in FIG. 7 is shown for example in FIG. 13. As can be seen in FIG. 13, the quill filament 20 has a first zone 30*a* with a plurality of quills 22, a second zone 30*b* with no quills, and a third zone 30*c* with a plurality of quills 22 where the second zone is between and connects the first and the third zones. The quill filaments each have the same orientation when incorporated into the stent. In some embodiments, the quills 22 in the first and third zones of the quill filament are facing the same direction relative to an end 11*a* of the filament. In other embodiments, the quills 22 in the first and third zones of the quill filament are facing opposite directions relative to an end of the filament (not shown). In one embodiment, this method results in an interwoven stent with a plurality of quills 22 oriented in the same direction relative to an end 11*a* of the stent 10, as shown for example in FIG. 7 and in the enlarged depiction of FIG. 3, as discussed above. Also as shown in FIG. 7, the stent 10 has quills 22 positioned in the end regions 12, 16 of the stent 10 but not in the middle region 14 of the stent 10.

In one embodiment, the stent 10 shown in FIG. 8 is made with a plurality of quill filaments 20 using a continuous braiding method where each quill filament 20 has a plurality of quills 22 along the length of the filament 20; each quill 22 on a filament 20 is facing the same direction; and the quill filaments 20 each have the same orientation when incorporated into the stent. This method results in an interwoven stent 10 with a plurality of quills 22 oriented in the same direction relative to an end 11*a* of the stent 10, as shown for example in FIG. 8 and in the enlarged depiction of FIG. 3, as discussed above.

In one embodiment, the stent 10 shown in FIG. 15 is made with a plurality of quill filaments 20 using a continuous braiding method where the plurality of quill filaments 20 include first quill filaments and second quill filaments where the orientation of the quills 22 on the first quill filaments is opposite the orientation of the quills 22 on the second quill filaments; wherein each first quill filament has the same orientation when incorporated into the stent and each second quill filament has the same orientation when incorporated into the stent, the orientations of the first and second quill filaments being opposite orientations when incorporated into the stent. This method results in an interwoven stent 10 with a plurality of quills 22 oriented in two opposite directions relative to each end 11*a* and 11*b* of the stent 10, as shown for example in FIG. 15. FIG. 1 is an enlarged depiction of a portion of a stent 10 comprising interwoven quill filaments 20 where the quills 22 of some of the quill filaments 20 are oriented in a first direction relative to an end 11 of the stent 10 and the quills 22 of other of the quill filaments 20 are oriented in a second direction, opposite to the first direction, relative to each end 11*a* and 11*b* of the stent 10. Thus, the tips 24 of some quill filaments 20 are directed away from a first end 11*a* of the stent 10 and towards the second end 11*b* of the stent 10 while the tips 24 of other quill filaments 20 are directed away from the second end 11*b* of the stent 10 and towards the first end 11*a* of the stent 10, as can be seen in the stent 10 provided in FIG. 15.

In another embodiment, the stent 10 shown in FIG. 9 is made with a plurality of quill filaments 20 using a continuous braiding method where each quill filament 20 comprises quills 22 that alternate between a first direction and a second direction along the length of the quill filament 20. This method results in an interwoven stent 10 with a plurality of quills 22 oriented in two opposite directions relative to each end 11*a* and 11*b* of the stent 10, as shown for example in FIG. 9. FIG. 2 is an enlarged depiction of a portion of a stent 10 comprising interwoven quill filaments where the direction of the quills 22 alternates between a first direction and a second direction along the length of the filament (D1-D2-D1-D2- . . . ). As can be seen in FIG. 2, for each quill filament 20, the tips 24 of some quills 22 are directed away from a first end 11*a* of the stent 10 and towards the second end 11*b* of the stent 10 while the tips 24 of other quills 22 are directed away from the second end 11*b* of the stent 10 and towards the first end 11*a* of the stent 10.

In one embodiment, the stent 10 shown in FIG. 10 is made with a plurality of quill filaments 20 using a discrete braiding method with quill filaments 20 each having the same orientation when incorporated into the stent. This method results in an interwoven stent 10 with a plurality of quills 22 oriented in the same direction relative to an end 11*a* of the stent 10, as shown for example in FIG. 10. In some embodiments, the ends of the quill filaments 20 are welded or otherwise bonded one to another to form the other end of the stent 10 (not shown). An example of a quill filament 20 of the stent shown in FIG. 10 is shown in FIG. 11. As can be seen in FIG. 11, each quill filament 20 has a first zone 30*a* with quills 22 oriented in a first direction relative to the first end 11*a* of the quill filament, and a third zone 30*c* with quills 22 oriented in a second direction relative to the first end 11*a* of the quill filament where the second direction is opposite to the first direction. The second zone 30*b* of each quill filament 20 forms a loop 36 at one end of the stent 10. In one embodiment, the second zone 30*b* forms a middle portion of the filament.

Although FIGS. 5-10 and 15 show stents made entirely of quill filaments, as discussed above, it is within the scope of the invention for a portion of the interwoven strands to be quill filaments and a portion of the interwoven strands to be non-quill filaments. The combination of quill filaments and non-quill filaments can be interwoven using the methods discussed above or by any other suitable method.

In at least one embodiment, the quill filaments are interwoven by weaving. A schematic example of a stent 10 made by weaving quill filaments 20 is shown in FIG. 14. In some embodiments, a plurality of quill filaments 20 is interwoven with a plurality of filaments without quills to form a stent with a plurality of quills 22. In one embodiment, the quill filaments 20 are arranged longitudinally relative to the longitudinal axis of the stent and the non-quill filaments are arranged circumferentially relative to the longitudinal axis of the stent 10. Thus, the quill filaments 20 are at about a 90 degree angle relative to the non-quill filaments. In this embodiment, the orientation of the quills 22 is substantially parallel to the longitudinal axis of the stent 10.

As shown for example in the enlarged depiction of FIG. 4, the bases 28 of the quills 22 do not have the same position on the filament but the position of the bases of the quills 22 overlap so that at least one axis bisects the bases on the filament so that the quills 22 have substantially the same orientation. As shown in FIG. 4, the orientation is substantially parallel to the axis (A). In some embodiments, the quills 22 are each oriented in the same direction relative to an end 11a of the stent. In other embodiments, the quills 22 are oriented in opposite directions relative to an end 11 of the stent. In one embodiment, a first group of quills 22 is oriented in a first direction relative to a first end of the stent, and a second group of quills 22 is oriented in a second direction relative to a first end of the stent, where the first and second directions are opposite directions.

As discussed above, it is within the scope of the invention for the all of the quills of a stent to be oriented in the same direction relative to an end of the stent or for some of the quills of a stent to be oriented in a first direction and others of the quills of to be oriented in a second direction different than the first direction. Also as discussed above, at least one portion of the stent has quills.

In some embodiments, the quills are only located on one side of the filament. In other embodiments, the quills are located all around the filament circumference, as shown for example in FIG. 16. This is especially useful when the filaments are quilled before the forming the stent because it ensures that at least part of the quills are positioned on the exterior surface of the stent in order to provide anchoring when the stent is implanted in a body lumen.

In other embodiments, at least one quill filament 20 is attached to a stent 10. The stent 10 to which a quill filament is attached may be created by any suitable method. Non limiting examples of methods to form the stent 10 include cutting or etching a design from a tubular stock; from a flat sheet which is cut or etched and which is subsequently rolled; or from one or more interwoven wires or braids. The framework of the stent can have pattern and comprise a plurality of elements such as, but not limited to, struts, connectors, and turns.

It is within the scope of the invention for a stent framework with at least one quill filament attached or secured thereto to have the orientations and placement as shown in FIGS. 5-9 and 14-15. The quill filaments attached to the framework of the stent can have the configurations shown in FIGS. 11-13 and 16 or other suitable configurations, e.g. quills along the entire length of the filament facing the same direction. The quill filament 20 can be attached or secured to the stent framework in any manner, for example but not limited to, welding, soldering, brazing, wrapping, interweaving, and any combination thereof.

FIG. 4 is an example of a portion of a framework of a stent 10 to which a quill filament 20 has been attached thereto. In one embodiment, the quill filament 20 is attached to the outer surface of the framework of the stent 10. In at least one embodiment, the quill filament 20 is substantially parallel to the longitudinal axis of the stent. In some embodiments, the quill filament is wrapped onto the framework of the stent. For example, the quill filament is wrapped around at least some of the elements of the stent framework so that the quill filament is contacts all sides of an element of the stent framework. In other embodiments, the quill filament is interwoven with the framework. For example, the quill filament is woven in and out of the cells defined by the stent framework and the ends of the quill filament are secured to the framework of the stent. In this embodiment, the quill filament contacts only one side of the element of the stent framework. In some embodiments, wrapping the quill filament around the stent framework provides more quills per area than interweaving the quill filament to the stent framework.

Although in some embodiments, the quills of a stent are compressed during delivery of the stent to a body lumen, the quills return to the oblique angle once the stent is withdrawn from the delivery device. In at least one embodiment, the stent may be loaded in the delivery device just before implantation to ensure that there is no relaxation of the quills due to compression in a delivery device.

With regard to the quill filaments used in the stents described above, in some embodiments the quill 22 is formed by skiving or shaving the filament using any suitable method thereby forming a quill 22 that has a base 28, a tip 24, and a body 26. The quill 22 is integral with and remains attached to the filament with the quill being at an oblique angle relative to the filament. Thus, the quill extends over the surface of the filament. In some embodiments, the oblique angle is about 5° to about 30° relative to the surface of the filament. Another way to view the formation of the quill filament is that a filament with an outer surface is modified to have a plurality of extensions of filament material at an angle to the outer surface where the weight of the filament is substantially the same with or without the extensions of filament material.

The body 26 of the quill 22 has a length measured from the base 28 to the tip 24. In some embodiments, the quill 22 has a length from the base 28 to the tip of about 0.5 mm to about 2 mm. The quill 22 has a top surface, which was the surface of the filament, and a bottom surface. The shape of the top surface of the quill 22 is the same as the shape of the outer surface of the filament before the quill was formed. In some embodiments, the bottom surface of the quill 22 is substantially flat. In some embodiments, the quill 22 has a variable width with the base 28 being wider than the tip 24. In some embodiments, the quill 22 has a width at the base 28 of about 0.1 mm to about 0.5 mm and a width at the tip 24 of about 0.05 mm to about 0.1 mm. The direction from the base 28 to the tip 24 of the quill 22 is the direction of the quill 22. As shown in the figures, the quill 22 is attached to the filament 20 by the base 28 of the quill 22. In some embodiments, the quill 22 is a variable distance away from the surface of the filament 20, with the base 28 being attached to the surface of the filament, the tip 24 being a distance away from the surface of the filament, and the body 26 extending at an oblique angle, relative to the surface of the filament, from the base 28 to the tip 24. In some embodiments, the tip 24 of the quill 22 is about 0.2 mm to about 1 mm above the surface of the filament 20.

Adjacent quills 22 on a filament are separated one from another by about 1 mm to about 5 mm. Thus, the tip 24 on one quill 22 is about 0.5 mm to about 4.5 mm away from the base 28 of the adjacent quill 22. This distance can be considered a separation distance along the longitudinal dimension of the filament. However as shown in FIG. 16, the quills 22 may also be offset along the circumference of the filament.

It is within the scope of the invention for the quills 22 on a filament to have any frequency of occurrence along the length of the filament. In some embodiments, the filament has 1 quills per cm of filament length to 10 quills per mm of filament length.

It is within the scope of the invention for the stent to have any frequency of occurrence of quills along a length of the stent. In some embodiments, the stent has 5 quills per cm of stent length to 100 quills per cm of stent length.

The quill 22 can be formed by any suitable method. For example, a blade or a laser can be used to form the quill. It is within the scope of the invention for the quills to be formed on a filament before or after the filament has been attached to, or interwoven to form, a stent. In some embodiments, quills are formed along the entire length of the filament. In other embodiments, the quill filament 20 has a plurality of zones 30 where some zones have quills 22 and other zones are quill-free. It is within the scope of the invention for each zone 30 of a quill filament 20 to have any length. In some embodiments, each zone 30 has the same length. In other embodiments, the zones 30 of a quill filament 20 have different lengths. In at least one embodiment, each quill filament 20 only has three zones 30 where the property of a zone is different than the adjacent zone. For example, as discussed with regard to the non-limiting examples above, it is within the scope of the invention for the quills in a zone of a quill filament to have the same orientation or different orientations relative to the quills in another zone. It is also within the scope of the invention for the orientation of the quills in one zone to have the same or different orientation than the quills in another zone of the quill filament.

In at least one embodiment, a stent 10 with a plurality of quills 22 is made by forming a stent 10 and then by forming a plurality of quills 22 on at least one portion of the stent 10. In this embodiment, the quills 22 are formed on the stent 10 using the methods described above for making quills on a filament. In some embodiments, the quills are formed on a stent 10 on a mandrel.

The inventive stents 10 and/or quill filaments 20 may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The inventive stents 10 and/or quill filaments 20 may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

In some embodiments the stent 10, the quill filament 20, the delivery system, or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent 10 and/or quill filament 20 is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The following numbered statements characterize at least some of the embodiments described above:

1. A stent, the stent comprising a plurality of interwoven quill filaments extending from a first end to a second end of the stent, each quill filament comprising filament material, a surface, and a plurality of quills, each quill having a tip, a body, and a base, the body extending from the base to the tip, wherein at least a portion of the stent comprises quills, each quill oriented in a first direction relative to the first end of the stent.
2. The stent of statement 1, wherein each quill filament comprise a first zone, a second zone, and a third zone, the second zone extending between and connected to the first and third zones, wherein the first zone comprises a plurality of quills, the third zone comprises a plurality of quills, the second zone has no quills, the quills of the first zone and the quills of the third zone facing the same direction relative to an end of the quill filament.
3. The stent of statement 2, the second zone of each quill filament forming a loop at an end of the stent.
4. The stent of statement 1, wherein each quill filament comprise a first zone, a second zone, and a third zone, the second zone between and connected to the first and third zones, wherein only the second zone comprises a plurality of quills.
5. The stent of statements 1-4, the stent comprising a first end region, a second end region, and a middle region between the first and second end regions, at least one of the first end region, the second end region, and the middle region being the at least a portion of the stent comprising quills.
6. The stent of statement 5, wherein only the middle region of the stent comprises quills.
7. The stent of statement 5, wherein only the first end region and the second end region of the stent comprises quills.
8. The stent of statement 5, wherein each of the first end region, the second end region, and the middle region of the stent comprises quills.
9. The stent of statements 1-8, wherein the first end region and the second end region of the stent are flared relative to the middle region of the stent.
10. The stent of statements 1-9, the quill filaments having 1 quill per cm of filament length to 10 quills per cm of filament length.
11. The stent of statements 1-10, the stent having 5 quills per cm of stent length to 100 quills per cm of stent length.
12. The stent of statements 1-11, each quill having a being at an angle relative to the surface of the quill filament, wherein the angle is about 5° to about 30°.
13. The stent of statements 1-12, each quill having a length of about 0.5 mm to about 2 mm.
14. The stent of statements 1-13, each quill having a variable width wherein a width at the base being greater than a width at the tip.
15. The stent of statement 14, wherein the width at the base of the quill is about 0.1 mm to about 0.5 mm and the width at the tip of the quill is about 0.05 to about 0.1 mm.
16. The stent of statements 1-15, wherein the tip of a quill is positioned about 0.2 mm to about 1 mm above the surface of the quill filament.
17. The stent of statements 1-16, wherein the tip of one quill is about 0.5 mm to about 4.5 mm from the base of an adjacent quill.
18. A stent, the stent comprising a plurality of interwoven quill filaments extending from a first end to a second end of the stent, each quill filament comprising filament material, a surface, and a plurality of quills, each quill having a tip, a body, and a base, the body extending from the base to the tip, wherein at least a portion of the stent comprises quills, the stent having a plurality of first quills each oriented towards the first end of the stent and a plurality of second quills each oriented towards the second end of the stent.
19. The stent of statement 18, wherein each quill filament comprise a first zone, a second zone, and a third zone, the second zone extending between and connected to the first and third zones, wherein the first zone comprises a plurality of quills, the third zone comprises a plurality of quills, the second zone has no quills, the quills of the first zone and the quills of the third zone facing the same direction.
20. The stent of statement 19, the second zone of each quill filament forming a loop at an end of the stent.
21. The stent of statement 18, wherein each quill filament comprise a first zone, a second zone, and a third zone, the second zone between and connected to the first and third zones, wherein only the second zone comprises a plurality of quills.
22. The stent of statements 18-21, the stent comprising a first end region, a second end region, and a middle region between the first and second end regions, the at least a portion of the stent comprising quills being at least one of the first end region, the second end region, and the middle region
23. The stent of statement 22, wherein only the middle region of the stent comprises quills.
24. The stent of statement 22, wherein only the first end region and the second end region of the stent comprises quills.
25. The stent of statement 22, wherein each of the first end region, the second end region, and the middle region of the stent comprises quills.
26. The stent of statements 18-25, wherein the first end region and the second end region of the stent are flared relative to the middle region of the stent.
27. The stent of statements 18-26, the quill filaments having 1 quill per cm of filament length to 10 quills per cm of filament length.
28. The stent of statements 18-27, the stent having 5 quills per cm of stent length to 100 quills per cm of stent length.
29. The stent of statements 18-28, each quill having a being at an angle relative to the surface of the quill filament, wherein the angle is about 5° to about 30°.
30. The stent of statements 18-29, each quill having a length of about 0.5 mm to about 2 mm.
31. The stent of statements 18-30, each quill having a variable width wherein a width at the base being greater than a width at the tip.
32. The stent of statement 31, wherein the width at the base of the quill is about 0.1 mm to about 0.5 mm and the width at the tip of the quill is about 0.05 to about 0.1 mm.
33. The stent of statements 18-32, wherein the tip of a quill is positioned about 0.2 mm to about 1 mm above the surface of the quill filament.
34. The stent of statements 18-33, wherein the tip of one quill is about 0.5 mm to about 4.5 mm from the base of an adjacent quill.
35. A stent, the stent comprising a framework and at least one quill filament engaged to the framework.
36. The stent of statement 35, wherein the at least one quill filament is engaged to the framework by wrapping, adhesive, welding, interweaving, and combinations thereof
37. The stent of statements 35-36, the quill filaments having 1 quill per cm of filament length to 10 quills per cm of filament length.
38. The stent of statements 35-37, the stent having 5 quills per cm of stent length to 100 quills per cm of stent length.
39. The stent of statements 35-38, each quill having a being at an angle relative to the surface of the quill filament, wherein the angle is about 5° to about 30°.
40. The stent of statements 35-39, each quill having a length of about 0.5 mm to about 2 mm.
41. The stent of statements 35-40, each quill having a variable width wherein a width at the base being greater than a width at the tip.

42. The stent of statement 41, wherein the width at the base of the quill is about 0.1 mm to about 0.5 mm and the width at the tip of the quill is about 0.05 to about 0.1 mm.

43. The stent of statements 35-42, wherein the tip of a quill is positioned about 0.2 mm to about 1 mm above the surface of the quill filament.

44. The stent of statements 35-43, wherein the tip of one quill is about 0.5 mm to about 4.5 mm from the base of an adjacent quill.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. An interwoven stent comprising a middle stent region between two end stent regions and quills oriented towards a first stent end, wherein the middle stent region is quill free, each quill integral with a quill filament, the stent comprising a plurality of quill filaments,
   wherein only the two end stent regions have quills, and
   wherein each quill filament comprises a first zone, a second zone, and a third zone, the second zone connecting the first and third zones, each quill filament having quills only in the first and third zones.

2. The stent of claim 1, the quill filaments having a same orientation when incorporated into the stent.

3. The stent of claim 1, wherein quills in the first and third zones face a first filament end.

4. The stent of claim 1, the stent further comprising quills oriented towards a second stent end, wherein the quills of the first zone face a first filament end, and the quills of the third zone face a second filament end.

5. The stent of claim 1, the stent further comprising a cover, wherein the quills engage the cover.

6. A stent comprising interwoven quill filaments, each quill filament having quills, the quills including first quills oriented towards a first filament end, and second quills oriented towards a second filament end, the quills alternating between first quills and second quills, the stent having quills oriented towards each stent end,
   wherein the interweaving of quill filaments defines successive intersections between quill filaments, and
   wherein when a quill selected from the first quills or the second quills is present between successive intersections of quill filaments only one quill is present between successive intersections of quill filaments.

7. The stent of claim 6, the stent comprising a middle stent region between two end stent regions, the two end stent regions having a larger diameter than the middle stent region.

8. The stent of claim 6, the stent further comprising a cover, wherein the quills engage the cover.

9. The stent of claim 6, the stent having no looped ends.

* * * * *